United States Patent

Muff

Patent Number: 5,476,493
Date of Patent: Dec. 19, 1995

[54] IMPLANTABLE LEAD HAVING SELF-LOCKING SUTURE SLEEVE

[75] Inventor: Diane M. Muff, Granada Hills, Calif.

[73] Assignee: Pacesetter, Inc., Sylmar, Calif.

[21] Appl. No.: 64,681

[22] Filed: May 19, 1993

[51] Int. Cl.⁶ ........................ A61N 1/05
[52] U.S. Cl. ........................ 607/119; 604/175
[58] Field of Search .............. 607/119, 132; 128/642, 639; 604/171, 174, 175, 178, 180

[56] References Cited

U.S. PATENT DOCUMENTS

| | | | |
|---|---|---|---|
| 3,509,883 | 5/1970 | Dibelius | 128/348 |
| 4,122,858 | 10/1978 | Schiff | 604/175 |
| 4,276,882 | 7/1981 | Dickhudt et al. | 128/419 P |
| 4,387,727 | 6/1983 | Sandstrom | 128/784 |
| 4,516,584 | 5/1985 | Garcia | 128/785 |
| 4,526,572 | 7/1985 | Donnan et al. | 604/29 |
| 4,538,623 | 9/1985 | Proctor et al. | 128/784 |
| 4,553,961 | 11/1985 | Pohndorf et al. | 604/175 |
| 4,629,455 | 12/1986 | Kanno | 604/241 |
| 4,650,473 | 3/1987 | Bartholomew et al. | 604/174 |
| 4,672,979 | 6/1987 | Pohndorf | 128/784 |
| 4,676,782 | 6/1987 | Yamamoto et al. | 604/175 |
| 4,683,895 | 8/1987 | Pohndorf | 128/784 |
| 4,906,233 | 3/1990 | Moriuchi et al. | 604/174 |
| 4,944,088 | 7/1990 | Doan et al. | 29/858 |
| 5,107,856 | 4/1992 | Kristiansen et al. | 607/132 |
| 5,257,975 | 11/1993 | Foshee | 604/175 |
| 5,273,053 | 12/1993 | Pohndorf | 607/132 |

FOREIGN PATENT DOCUMENTS 1308572  7/1988  Japan ............... A61M 25/02

Primary Examiner—William E. Kamm
Assistant Examiner—Marianne Parker
Attorney, Agent, or Firm—Lisa P. Weinberg; Harold C. Schloss

[57] ABSTRACT

A movable self-locking suture sleeve which can be securely positioned on the lead body of a pacing lead. The self-locking suture sleeve includes first and second cooperative rigid elements interconnected by a flexible tubing element. The tubing element is constructed from a woven mesh designed to constrict when stretched. A resilient element or spring is interposed between the first and second cooperative rigid elements, tending to force the cooperative rigid elements axially apart. Once the suture sleeve is moved into position, a self-locking feature allows the suture sleeve to secure itself to the lead body.

37 Claims, 2 Drawing Sheets 5,476,493

IMPLANTABLE LEAD HAVING SELF-LOCKING SUTURE SLEEVE

FIELD OF THE INVENTION

The present invention relates generally to an implantable pacing lead for use with a cardiac pacemaker, and more specifically to a pacing lead having a self-locking suture sleeve for securing the placement of the lead at the point of venous insertion.

BACKGROUND OF THE INVENTION

A number of types of implantable leads for use with a cardiac pacemaker and/or defibrillator to form a pacing system are known in the art. Some leads require transvenous insertion and have a portion of the lead body inserted into the vein and extending into the heart. The remainder of the lead body which is not inserted into the vein extends to a point of attachment to an implanted pacemaker. The leads generally include at least one electrode which is implanted at a particular location within the heart. The implant location is particularly critical in order to allow optimum system performance. Thus, it is imperative that the electrode, and thus the lead body, are securely positioned in order to prevent dislodging of the implanted electrode after implantation.

Accordingly, it is common to utilize a suture sleeve, located about a portion of the lead body, which is secured to tissue in such a manner that the potential for displacement of the lead body is minimized. Generally, the suture sleeve is positioned proximate the point of venous insertion. Various types of suture sleeves have been used in the art, including sleeves which are integrally formed with the lead body and thus stationary in their location, and suture sleeves which can be slidably positioned axially along at least a limited portion of the length of the lead body. The primary advantage of the suture sleeves which may be slidably positioned along the lead body is that the lead may be implanted in patients having a range of physical dimensions, and the suture sleeve may be positioned appropriately.

Generally, the suture sleeve is positioned proximate the point of venous insertion and secured to the lead body using suture material and a suture tie. The suture sleeve is then secured to the surrounding tissue using a suture needle and suture thread. The suture sleeve preferably includes a slot which allows the attending physician to wrap the suture thread around and over the suture sleeve a number of times, each time securing the thread to the adjacent tissue.

A recurring problem with the use of suture sleeves to secure the lead body results from the potential for the attending physician to overtighten the suture thread about the suture sleeve, thereby crushing the electrical conductors or insulation extending through the lead body. For most lead body applications, the electrical conductors extending between the proximal and distal ends are formed into a helix defining a central open core. The benefit of the helical conductors is that the lead body is highly flexible yet durable. The disadvantage which results is the potential for flattening or crushing of the helix, thereby incurring localized stresses within the conductors which may cause parting of the conductors or breakage of insulation resulting in failure of the lead.

Accordingly, it would be desirable to have a suture sleeve which is both adjustable along a portion of the length of the lead body but which prevents or minimizes the risk of damage to the electrical conductors or insulation of the lead caused by overtightened anchoring sutures. While the adjustable feature of the suture sleeve is desirable, the suture sleeve should also be designed to secure the axial location of the lead body once the position of the suture sleeve is fixed. Suture sleeves of the prior art which are slidably positionable yet structurally rigid enough to prevent the suture threads from damaging the conductors are not easily secured to the lead body.

SUMMARY OF THE INVENTION

The present invention contemplates a pacing lead having a movable self-locking suture sleeve which can be securely positioned on the lead body. Specifically, once the suture sleeve is moved into position, a self-locking feature allows the suture sleeve to secure itself to the lead body. In addition, once the position of the suture sleeve is secured, the attending physician can suture the suture sleeve to the surrounding tissue with a reduced potential for causing damage to the conductors extending through the lead body.

The self-locking suture sleeve includes a flexible tubing element affixed at either end of the suture sleeve body. The tubing element is constructed from a woven mesh designed to constrict when stretched. A resilient element or spring biases the tubing element, tending to force the tubing element to its fully stretched position. The spring and tubing element cooperate such that when the spring is compressed, the tubing element has a maximum diameter and the suture sleeve is slidable along the lead body which extends axially through the center of the self-locking suture sleeve. When the spring is expanded to its relaxed state, the tubing element constricts, securely grasping the lead body.

In the preferred embodiment, the suture sleeve body includes a first and a second cooperative rigid elements interconnected by the flexible tubing element. The resilient element or spring is interposed between the first and second cooperative rigid elements, tending to force the cooperative rigid elements axially apart. By forcing the first and second rigid elements together, the tubing element has a maximum diameter and the suture sleeve is slidable along the lead body which extends axially through the center of the self-locking suture sleeve. By releasing the spring, the first and second rigid elements are displaced apart axially and the tubing element constricts, securely grasping the lead body.

In an alternate embodiment, the resilient element or spring could be formed within the tubing element itself.

DETAILED DESCRIPTION OF THE PREFERRED EMBODIMENT

Figure 1:
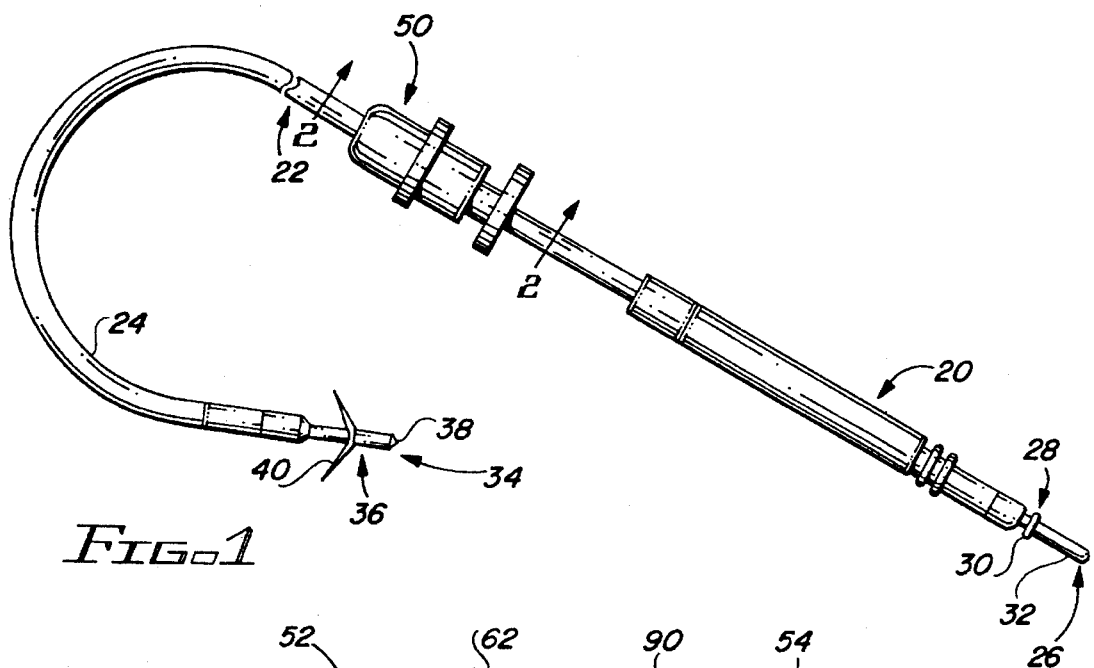
FIG. 1 depicts a pacing lead including a self-locking suture sleeve according to the present invention.

FIG. 1 shows a plan view of a pacing lead 20 according to the present invention. The pacing lead 20 has an elongated lead body 22 which includes electrical conductors (not shown) contained within an insulation sheath 24. The insulation sheath 24 is preferably a flexible, biocompatible material, such as silicone rubber, polyurethane, or a suitable plastic. At a proximal end 26 of the pacing lead 20 is a connector assembly 28, which is provided with sealing rings 30 and which carries at least one electrical terminal 32. The connector assembly 28 is constructed using known techniques and the non-conductive portions are preferably fabricated of silicone rubber, polyurethane, or a suitable plastic. The electrical terminal 32 is preferably fabricated of a stainless steel or other suitable conductive material, and is connected to the electrical conductor extending through the lead body 22.

At a distal end 34 of the pacing lead 20 is located an electrode assembly 36. The electrode assembly 36 may include an electrode 38 and a plurality of anchoring tines 40. The electrode 38 is designed to abut against endocardial tissue, and the tines 40 tend to secure the placement of the electrode 38. The electrode assembly 36 can include a number of additional elements, such as additional electrodes or alternative configurations for the electrode 38. A number of designs for the electrode 38 and electrode assembly 36 are well known. Each electrode which is included in the electrode assembly 36 is interconnected to at least one electrical conductor (not shown) extending through the lead body 22 to the connector assembly 28.

Positioned along the length of the lead body 22, intermittent the connector assembly 28 and the electrode assembly 36, is a self-locking suture sleeve 50 in accordance with the present invention. The self-locking suture sleeve 50 is designed to be movable axially along the lead body 22, to allow positioning at a point suitable for affixation to tissue.

Figure 2:
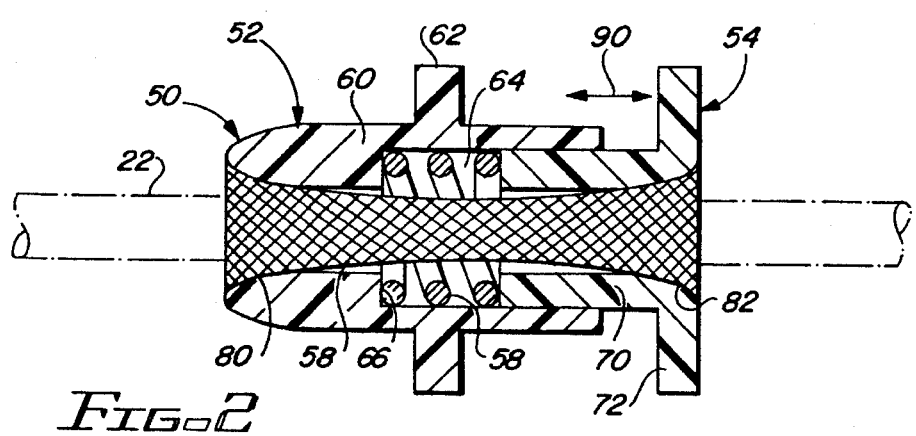
FIG. 2 depicts a cross sectional view of the self-locking suture sleeve.
Figure 3:
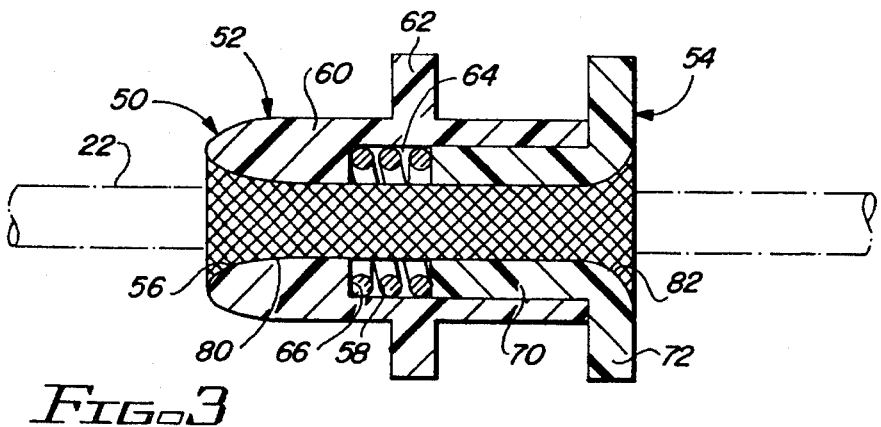
FIG. 3 depicts a second cross sectional view of the self-locking suture sleeve of FIG. 2.
Figure 4:
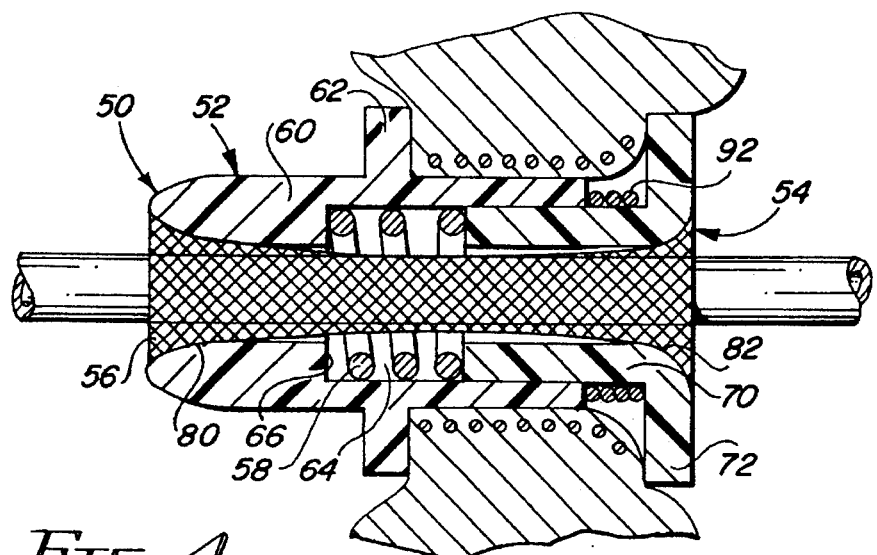
FIG. 4 depicts a cross sectional view of the self-locking suture sleeve of FIGS. 2 or 3 positioned about the lead body of the pacing lead of FIG. 1 and sutured to tissue.

The details of the design of the self-locking suture sleeve 50 are illustrated in the cross sectional views of FIGS. 2–4, wherein like numbers refer to like elements. In the preferred embodiment, the self-locking suture sleeve 50 includes four primary components: a first rigid element 52, a second rigid element 54, coaxially mounted with the first rigid element 52, a cylindrical tubing element 56, and a resilient expansion element illustrated as a spring 58.

The following detailed description of the first rigid element 52 and second rigid element 54 is intended to illustrate a particular design in which these elements may be configured. However, it is to be understood that following review of the entire specification, it will be apparent that a number of alternative designs for the first rigid element 52 and second rigid element 54 will be readily apparent to those skilled in the art. For example, the tubing element could have resilient means woven within the mesh and/or shaped so that the rigid elements could be eliminated. Accordingly, the description is only intended to be illustrative of the preferred embodiment and best mode of the invention.

The first rigid element 52 includes a generally cylindrical portion 60 and a radially extending flange 62. The internal diameter of the generally cylindrical portion 60 includes a recessed area 64 extending from the end facing the second rigid element 54 axially inward along the cylinder, to define a step 66 located within the inner cylindrical cross section of the axial length of the first rigid element 52.

The second rigid element 54 may simply include a cylindrical portion 70 and flange portion 72 interconnected to an end of the cylindrical portion 70. The cylindrical portion 70 is configured in size to be axially inserted at least partially into the recessed area 64 of the first rigid element 52.

The spring 58 is positioned within the recessed area 64 such that one end of the spring 58 abuts against the internal step 66 of the first rigid element 52, and the other end of the spring 58 abuts against an end of the cylindrical portion 70 of the second rigid element 54. The spring 58 is positioned to tend to force the first rigid element 52 and second rigid element 54 axially apart when the spring 58 is expanded to its relaxed state.

Tubing element 56 extends axially through the center of the self-locking suture sleeve 50, and more particularly through the coaxial portions of the internal bores of the cylindrical portion 60 of the first rigid element 52 and cylindrical portion 70 of the second rigid element 54. The tubing element 56 is preferably secured at its ends 80 and 82, to the internal walls of the cylindrical portion 60 of first rigid element 52 and cylindrical portion 70 of second rigid element 54, respectively. The tubing element 56 is preferably designed such that the diameter of the tubing element 56 constricts when the tubing element 56 is subjected to an axial tension or torsional rotation.

The tubing element 56 may be formed from an appropriate biocompatible resilient plastic or elastomeric material such as silicone tubing, or alternatively, from a woven fibrous or stranded material. However, it is important that the materials used for the tubing element 56 be biocompatible, and stable for extend implanted durations. Thus, a woven mesh of high strength polymeric fibers or metallic strands is desirable. Suitable materials for the woven mesh include polymers such as polyester and nylon, as well as non-polymeric materials such as stainless steel, titanium and similar metallic materials. In addition, the first and second rigid elements 52 and 54 respectively, are preferably fabricated from a rigid biocompatible material. Suitable materials include stainless steel, titanium, plastics such as polyurethane, and rigid silicon.

As illustrated in FIG. 2, the spring 58 is depicted in a relaxed state, and the middle portion of the tubing element 56 is stretched and constricted, such that the diameter of the passageway axially through the center of the tubing element 56 is reduced. By comparison, the cross sectional view of FIG. 3 depicts the spring 58 in a compressed state, such that the total axial length of the first rigid element 52 and the second rigid element 54 is at a minimum, and the diameter of the tubing element 56 is at a maximum. In this spring-compressed state, the self-locking suture sleeve 50 is slidable over the lead body 22 of the lead 20. Upon proper positioning of the self-locking suture sleeve 50 on the lead body 22, the spring 58 is allowed to expand to its relaxed state, thereby causing the tubing element 56 to constrict and lock the position of the self-locking suture sleeve 50 about the lead body 22. Accordingly, it may be appreciated that the constriction of the tubing element 56 causes a secure frictional bonding to the insulation sheath 24 of the lead body 22, and prevents axial dislocation of the self-locking suture sleeve 50.

Once the lead 20 is properly implanted and the self-locking suture sleeve 50 is positioned, the attending physician can wrap the suture thread in the gap bounded by the flange 62 of the first rigid element 52, and flange 74 of the second rigid element 54. It should be noted that suture threads laid about the outer diameter of the cylindrical element 70 of the second rigid element 54, i.e. between the end of the first rigid element 52 and the flange 72 of the second rigid element 54 could also be used to prevent re-compression of the spring 58, which would allow expansion of the tubing element 56 and sliding of the self-locking suture sleeve 50 axially along the lead body 22.

As illustrated in FIG. 4, the lead 20 is implanted with the self-locking suture sleeve 50 positioned about a portion of the lead body 22 passing axially through the center of the tubing element 56. The self-locking suture sleeve 50 is secured by suture threads 92 which, in part, are depicted as being wrapped in the gap 90 between the flange 62 of first rigid 52 and the flange 72 of the second rigid element 54. The rigid structure of the first rigid element 52 and second rigid element 54 prevents the compressive stress which is exerted by wrapping of the suture thread about the self-locking suture sleeve 50 from being transmitted to the conductors (not shown) extending through the lead body 22. It may further be appreciated that the mechanical bond between the outer diameter of the lead body 22 and the self-locking suture sleeve 50 is accomplished solely by the constriction of the tubing element 56. Due to the configuration of the cylindrical tubing element 56, this mechanical compressive force is exerted uniformly over the outer diameter of the lead body 22 and is distributed over the entire length of engagement, thereby preventing high localized stresses which could give rise to localized flattening of the lead body 22 and crushing of the helical conductors or insulation therein.

Figure 5:
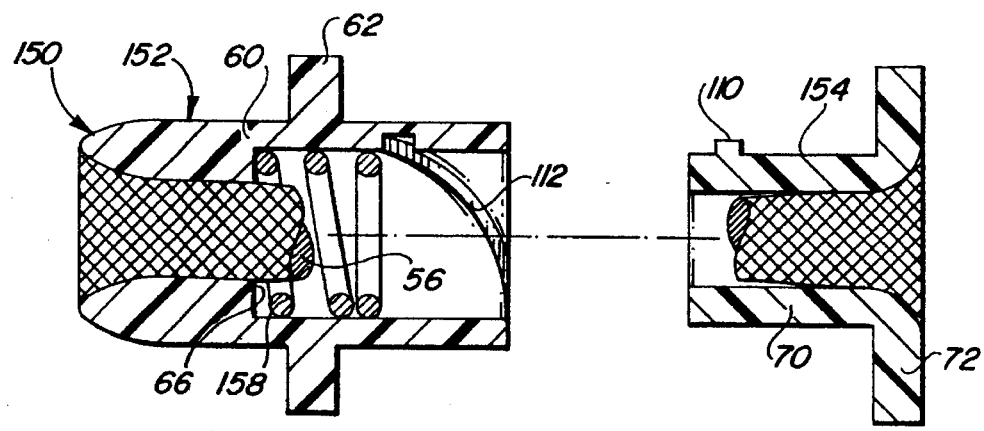
FIG. 5 depicts an exploded cross sectional view of an alternative embodiment for the self-locking suture sleeve.

An alternative embodiment of the present invention is depicted in the exploded cross-sectional view of FIG. 5. In FIG. 5, the first rigid element 152 and the second rigid element 154 are spaced apart by the action of a torsional spring 158, or alternatively the compressive spring 58 of FIGS. 2 and 3. A number of the structural components for the first and second rigid elements 152 and 154 are numbered similarly to the numbers in FIGS. 2–4. Rotational expansion of the torsional spring 158 causes relative rotation of the first rigid element 152 and second rigid element 154. Due to the affixation of the tubing element 56 to the ends of the first rigid element 152 and second rigid element 154 respectively, the relative rotation of the rigid elements 152 and 154 will cause a torsional twisting of the tubing element 56 which will constrict the tubing element 56 inner diameter, and cause the tubing element 56 to securely grasp the lead body (not shown).

It is further contemplated that guide means could be used in combination with the torsional spring 158 or that a compression spring such as 58 in FIG. 3 could be used, whereby the first rigid element 152 and second rigid element 154 are displaced both rotationally and axially upon expansion of the respective spring 158 or 58. Rotation and axial displacement of the rigid elements 152 and 154 will cause a constricting of the tubing element 56 about the lead body. The relative rotation may be accomplished simply by including a pin 110 extending radially outward from the cylindrical element 170 of second rigid element 154, which engages a helical groove 112 cut within the inner diameter of the cylindrical portion of the first rigid element 152. The cooperative interengagement of the pin element 110 and helical groove 112 will cause rotation of the rigid elements 152 and 154 as they expand axially apart.

Figure 6:
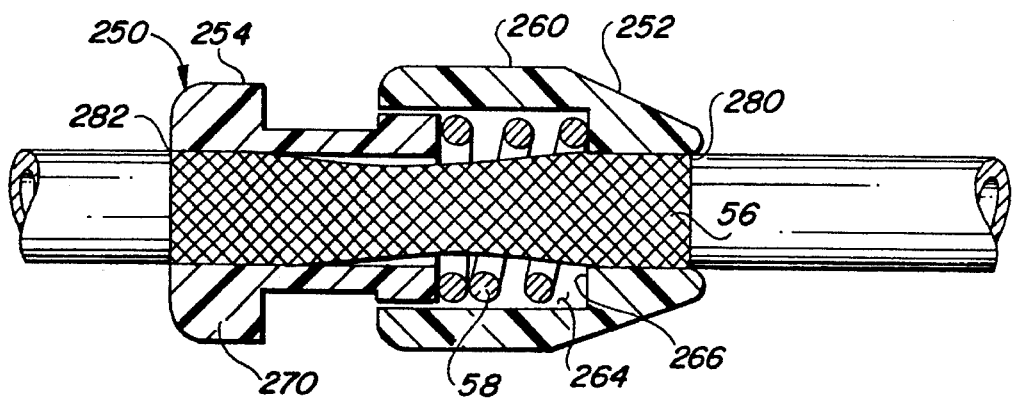
FIG. 6 depicts a cross sectional view of an alternate embodiment of the self-locking suture sleeve.

In an alternative embodiment, shown in FIG. 6, the self-locking suture sleeve 250 also includes four primary components: a first rigid element 252, a second rigid element 254, coaxially mounted with the first rigid element 252, a cylindrical tubing element 56, and a resilient expansion element illustrated as a spring 58.

The first rigid element 252 includes a generally cylindrical portion 260. The internal diameter of the generally cylindrical portion 260 includes a recessed area 264 extending from the end facing the second rigid element 254 axially inward along the cylinder, to define a step 266 located within the inner cylindrical cross section of the axial length of the first rigid element 252.

The second rigid element 254 may simply include a cylindrical portion 270 dimensioned to be axially inserted at least partially into the recessed area 264 of the first rigid element 252.

The spring 58 is positioned within the recessed area 264 such that one end of the spring 58 abuts against the internal step 266 of the first rigid element 252, and the other end of the spring 58 abuts against an end of the cylindrical portion 270 of the second rigid element 254. The spring 58 is positioned to tend to force the first rigid element 252 and the second rigid element 254 axially apart when the spring 58 is expanded to its relaxed state.

Tubing element 56 extends axially through the center of the self-locking suture sleeve 250, and more particularly through the coaxial portions of the internal bores of the cylindrical portion 260 of the first rigid element 252 and cylindrical portion 270 of the second rigid element 254. The tubing element 56 is preferably secured at its ends 280 and 282, to the internal walls of the cylindrical portion 260 of first rigid element 252 and cylindrical portion 20 of second rigid element 254, respectively.

As illustrated in FIG. 6, the spring 58 is depicted in a relaxed state position, and the middle portion of the tubing element 56 is stretched and constricted, such that the diameter of the passageway axially through the center of the tubing element 56 is reduced. When the suture sleeve 250 is in its spring-compressed state (not shown), the self-locking suture sleeve 250 is slidable over the lead body 22 of the lead 20. Upon proper positioning of the self-locking suture sleeve 250 on the lead body 22, the spring 58 is allowed to expand to its relaxed state, thereby causing the tubing element 56 to constrict and lock the position of the self-locking suture sleeve 250 about the lead body 22.

Upon review of the foregoing detailed description, it will be readily apparent to those skilled in the art that the present invention provides an improved self-locking suture sleeve for use with implantable leads. Moreover, based upon the foregoing detailed description, those skilled in the art will readily be able to design alternative configurations which will allow the placement of a constricting element, such as tubing element 56, within an suture sleeve to provide a self-locking anchoring feature for the suture sleeve on a lead body. Accordingly, while preferred embodiments have been herein disclosed and described, it is to be appreciated that the scope of the present invention is to be defined only by a proper literal and equivalent scope of the appended claims.

What is claimed is:

1. An implantable lead comprising:

a lead body extending between a proximal end and a distal end, the lead body having an outer diameter;

an electrical connector element positioned at the proximal end of the lead body;

an electrode assembly positioned at the distal end of the lead body; and a self-locking suture sleeve having a first end and a second end, the suture sleeve movable about at least a portion of the lead body between the proximal end and the distal end, the self-locking suture sleeve comprising:

a tubing element having a first end and a second end, the tubing element axially disposed about the outer diameter of the lead body, the tubing element first and second ends being affixed to respective ones of the ends of the self-locking suture sleeve;

means for elongating the tubing element so that the tubing element constrictably grips the lead body.

2. The implantable lead of claim 1, wherein the tubing element comprises a cylindrical woven mesh of biocompatible material, the mesh being woven so that the mesh has a smaller inner diameter when the mesh is elongated and a wider inner diameter when the mesh is compressed.

3. The implantable lead of claim 2, wherein the biocompatible material comprises a polymer material.

4. The implantable lead of claim 2, wherein the biocompatible material comprises a metallic material.

5. The implantable lead of claim 1, wherein the tubing element comprises a cylindrical element formed from a resilient, biocompatible elastomeric material.

6. The implantable lead of claim 1, wherein the elongating means comprises:

a resilient element coupled to the tubing element and operable between a relaxed state and a compressed state such that when the resilient element is in a compressed state the tubing element is in a relaxed state, and when the resilient element expands to its relaxed state the tubing element constricts.

7. The implantable lead of claim 6, wherein the resilient element comprises a spring element.

8. The implantable lead of claim 7, wherein the resilient element comprises a compression spring.

9. The implantable lead of claim 7, wherein the resilient element comprises a torsion spring.

10. The implantable lead of claim 6, wherein the self-locking suture sleeve further comprises:

a first housing means for receiving the tubing element, the first housing means having a generally cylindrical configuration including an internal bore, the first housing means further having a first end and a second end;

a second housing means for receiving the tubing element, the second housing means having a first end and a second end and having a generally cylindrical portion, the generally cylindrical portion having an outer diameter allowing at least partial insertion of the first end of the second housing means into the internal bore of the first housing means at the first end of the first housing means; and further wherein the tubing element is axially disposed about the outer diameter of the lead body, the tubing element being affixed at its first and second ends to the second ends of the first and second housing means respectively.

11. The implantable lead of claim 10, wherein the resilient element is a spring positioned to bias the first and second housing means so that when the resilient element is in a compressed state the tubing element is in a relaxed state, and when the resilient element expands to its relaxed state the tubing element constricts.

12. The implantable lead of claim 1, wherein the elongating means includes means for causing relative rotation of the first and second housing means.

13. The implantable lead of claim 12, wherein the means for causing relative rotation of the first and second housing means comprises a torsion spring.

14. The implantable lead of claim 12, wherein the means for causing relative rotation of the first and second housing means comprises:

a projecting element extending from a surface of the first housing means;

a helical groove formed within an adjacent surface of the second housing means, whereby said projecting element extends into and helically tracks the helical groove; and resilient means for biasing the first and second housing means causing relative motion therebetween.

15. The implantable lead of claim 12, wherein the means for causing relative rotation of the first and second housing means comprises:

a projecting element extending from a surface of the second housing means;

a helical groove formed within an adjacent surface of the first housing means, whereby said projecting element extends into and helically tracks the helical groove; and resilient means for biasing the first and second housing means causing relative motion therebetween.

16. An implantable lead comprising:

a lead body having an outer diameter; and a self-locking suture sleeve comprising:

a first rigid element having a generally cylindrical configuration including a stepped internal bore, the first rigid element having a first end and a second end;

a second rigid element having a generally cylindrical portion, the second rigid element having a first end and a second end, and having an outer diameter allowing at least partial insertion of the first end of the second rigid element into the internal bore of the first rigid element, at the first end of the first rigid element;

a tubing element axially disposed about the outer diameter of the lead body, the tubing element affixed at its first and second ends to the second ends of the first and second rigid elements respectively; and means for elongating the tubing element so that the diameter of at least a portion of the tubing element constricts about the lead body.

17. The implantable lead of claim 16, wherein the elongating means comprises:

a resilient element operable between a relaxed state and a compressed state, wherein when the resilient element is in a compressed state the tubing element is in a relaxed state, and when the resilient element expands to its relaxed state the tubing element constricts.

18. The implantable lead of claim 17, wherein the resilient element comprises a compression spring.

19. The implantable lead of claim 16, wherein the tubing element comprises a cylindrical woven mesh of biocompatible material.

20. The implantable lead of claim 19, wherein the biocompatible material comprises a polymer material.

21. The implantable lead of claim 19, wherein the biocompatible material comprises a metallic material.

22. The implantable lead of claim 16, wherein the tubing element comprises a cylindrical element formed from a resilient, biocompatible elastomeric material.

23. The implantable lead of claim 16, wherein the elongating means comprises:

means for causing relative rotation of the first and second rigid elements.

24. The implantable lead of claim 23, wherein the means for causing relative rotation of the first and second rigid elements comprises a torsion spring.

25. The implantable lead of claim 23, wherein the means for causing relative rotation of the first and second rigid elements comprises:

a projecting element extending from a surface of the first rigid element;

a helical groove formed within an adjacent surface of the second rigid element, whereby said projecting element extends into and helically tracks the helical groove; and resilient means for biasing the first and second rigid elements causing relative motion therebetween.

26. The implantable lead of claim 23, wherein the means for causing relative rotation of the first and second rigid elements comprises:

a projecting element extending from a surface of the second rigid element;

a helical groove formed within an adjacent surface of the second rigid element, whereby said projecting element extends into and helically tracks the helical groove; and resilient means for biasing the first and second rigid elements causing relative motion therebetween.

27. A method of securing an suture sleeve onto an implantable lead, the suture sleeve having a first end and a second end, and further having a cylindrical woven mesh of biocompatible material affixed to the first and second ends, the implantable lead comprising a lead body having an outer diameter, comprising the steps of:

placing the suture sleeve on the implantable lead whereby such that the cylindrical woven mesh of biocompatible material is axially disposed about the outer diameter of the lead body; and forcibly constricting at least a portion of the cylindrical woven mesh of biocompatible material, thereby frictionally securing the suture sleeve onto the lead body.

28. A method for forming a suture sleeve comprising the steps of:

forming a first rigid element having a generally cylindrical configuration including an internal bore, the first rigid element having a first end and a second end;

forming a second rigid element having a generally cylindrical portion, the second rigid element having a first end and a second end;

partially inserting the first end of the second rigid element into the internal bore of the first rigid element at the first end of the first rigid element;

affixing a first end and a second end of a cylindrical woven mesh of biocompatible material to the second ends of the first and second rigid elements respectively; and biasing the first and second rigid elements with a resilient element so that when the resilient element is forced into a compressed state the cylindrical woven mesh of biocompatible material is in a relaxed state and the suture sleeve is slidable about a lead body, and when the resilient element is released the cylindrical woven mesh of biocompatible material grips the lead body.

29. The method as recited in claim 28, wherein the biasing step comprises:

rotating the first and second rigid elements along a helical track thereby causing relative rotation therebetween.

30. An implantable lead comprising:

a lead body having an outer diameter, the lead body extending between a proximal end and a distal end;

an electrical connector element positioned at a proximal end of the lead body;

an electrode assembly positioned at the distal end of the lead body; and a self-locking suture sleeve movable about at least a portion of the lead body between the proximal end and the distal end the self-locking suture sleeve having a first end and a second end, the self-locking suture sleeve comprising:

a tubular woven mesh of biocompatible material axially disposed about the outer diameter of the lead body, the tubular woven mesh being affixed at its ends to the first and second ends of the self-locking suture sleeve, the tubular woven mesh having a smaller inner diameter when the tubular woven mesh is elongated and a wider inner diameter when the tubular woven mesh is compressed;

whereby the suture sleeve frictionally grips the lead body when the tubular woven mesh is elongated and enables the suture sleeve to slide when the tubular woven mesh is compressed.

31. The implantable lead of claim 30, wherein the biocompatible material comprises a polymer material.

32. The implantable lead of claim 30, wherein the biocompatible material comprises a metallic material.

33. The implantable lead of claim 30, wherein the self-locking suture sleeve further comprises:

a first cylindrical housing means for receiving the tubular woven mesh the first cylindrical housing means having an internal bore, a first end and a second end;

a second cylindrical housing means for receiving the tubular woven mesh, the second cylindrical housing means having a first end and a second end and further having an outer diameter dimensioned to fit within the internal bore of the first cylindrical housing means;

wherein the tubular woven mesh is affixed at its first and second ends to the second ends of the first and second cylindrical housing means respectively, the mesh being axially disposed about the outer diameter of the lead body; and a spring element positioned to bias the first and second cylindrical housing means so that when the spring element is in a compressed state the tubular woven mesh is in a relaxed state, and when the spring element is in its relaxed state the tubular woven mesh constricts.

34. The implantable lead of claim 33, wherein the spring element comprises a compression spring.

35. The implantable lead of claim 33, wherein the first and second cylindrical housing means comprise:

a projecting element extending from a surface of the first cylindrical housing means;

a helical groove formed within an adjacent surface of the second cylindrical housing means, whereby said projecting element extends into and helically tracks the helical groove; and wherein the spring element comprises a torsion spring for biasing the first and second cylindrical housing means causing relative motion therebetween.

36. The implantable lead of claim 33, wherein the spring element comprises a torsion spring.

37. The implantable lead of claim 33, wherein the first and second cylindrical housing means comprise:

a projecting element extending from a surface of the second cylindrical housing means;

a helical groove formed within an adjacent surface of the first cylindrical housing means, whereby said projecting element extends into and helically tracks the helical groove; and wherein the spring element comprises a torsion spring for biasing the first and second cylindrical housing means causing relative motion therebetween.

* * * * *